(12) United States Patent
Ryu et al.

(10) Patent No.: US 10,206,637 B2
(45) Date of Patent: Feb. 19, 2019

(54) INTEGRATED OPTICAL BLOCKING FILTER FOR COMPACT X-RAY IMAGING DETECTOR

(71) Applicant: Massachusetts Institute of Technology, Cambridge, MA (US)

(72) Inventors: Kevin K. Ryu, Arlington, MA (US); Peter W. O'Brien, Derry, NH (US); Marshall W. Bautz, Lexington, MA (US); Vyshnavi Suntharalingam, Carlisle, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 5 days.

(21) Appl. No.: 15/864,258

(22) Filed: Jan. 8, 2018

(65) Prior Publication Data

US 2018/0192974 A1  Jul. 12, 2018

Related U.S. Application Data

(60) Provisional application No. 62/443,887, filed on Jan. 9, 2017.

(51) Int. Cl.
| | | |
|---|---|---|
| *A61B 6/00* | (2006.01) |
| *G02B 5/20* | (2006.01) |
| *A61B 6/14* | (2006.01) |
| *A61B 5/00* | (2006.01) |
| *H01L 27/146* | (2006.01) |
| *G02B 5/22* | (2006.01) |
| *G02B 5/26* | (2006.01) |

(52) U.S. Cl.
CPC .......... *A61B 6/4035* (2013.01); *A61B 5/0059* (2013.01); *A61B 6/14* (2013.01); *G02B 5/208* (2013.01); *G02B 5/22* (2013.01); *G02B 5/26* (2013.01); *H01L 27/14683* (2013.01)

(58) Field of Classification Search
CPC ....... A61B 6/4035; A61B 5/0059; A61B 6/14; H01L 27/14683; G02B 5/208
USPC ..................................................... 250/370.09
See application file for complete search history.

(56) References Cited

U.S. PATENT DOCUMENTS

| | | | |
|---|---|---|---|
| 3,581,087 A | 5/1971 | Brinkerhoff et al. | |
| 6,608,628 B1 | 8/2003 | Ross et al. | |
| 6,697,453 B1* | 2/2004 | Mueller | G01N 23/207 |
| | | | 378/198 |

(Continued)

OTHER PUBLICATIONS

United States Patent and Trademark Office, International Search Report and Written Opinion for PCT/US18/12770 (corresponding PCT application) (dated May 30, 2018).

(Continued)

*Primary Examiner* — David P Porta
*Assistant Examiner* — Gisselle M Gutierrez
(74) *Attorney, Agent, or Firm* — Modern Times Legal; Robert J. Sayre

(57) ABSTRACT

An x-ray imaging device can include an x-ray detector and an optical-blocking filter. The x-ray detector has an entrance-window surface for receiving x-rays, at least one side surface, and a back surface facing in an opposite direction from the entrance-window surface. The optical-blocking filter is deposited on and fully covers at least the entrance-window surface and the side surface of the x-ray detector, wherein the optical-blocking filter blocks visible, ultraviolet, and near-infrared light.

20 Claims, 6 Drawing Sheets

(56) References Cited

U.S. PATENT DOCUMENTS

| | | | |
|---|---|---|---|
| 7,680,249 B2 | 3/2010 | Yuan | |
| 2009/0002968 A1* | 1/2009 | Li | A61B 6/06 361/818 |
| 2011/0007869 A1 | 1/2011 | Gendreau et al. | |
| 2012/0025089 A1 | 2/2012 | Takagi et al. | |
| 2014/0044240 A1* | 2/2014 | Pahlke | G21K 1/00 378/161 |
| 2015/0303024 A1 | 10/2015 | Harker et al. | |
| 2016/0231259 A1* | 8/2016 | Tanaka | G01N 23/2252 |

OTHER PUBLICATIONS

S. Granato, "The response of silicon PNCCD sensors with aluminum on-chip filter to visible light, UV- and X-ray radiation," Naturwissenschaftlich-Technische Fakultaet (2012).

A. D. Falcone, et al., "Recent progress on developments and characterization of hybrid CMOS x-ray detectors," Proceedings of SPIE (2012).

H. Tsunemi, et al., "In-Orbit Performance of the MAXI/SSC onboard the ISS," 62 Publ. Atron. Soc. of Japan 1371-79 (2010).

K. Ryu, et al., "Directly deposited optical-blocking filters for single-photon x-ray imaging spectroscopy," 3 J. Astron. Telesc. Instrum. Syst. 036001 (Jun. 28, 2017).

* cited by examiner

INTEGRATED OPTICAL BLOCKING FILTER FOR COMPACT X-RAY IMAGING DETECTOR

RELATED APPLICATION

This application claims the benefit of U.S. Provisional Application No. 62/443,887, filed 9 Jan. 2017, the entire content of which is incorporated herein by reference.

GOVERNMENT SUPPORT

This invention was made with government support under Grant NNX12AF22G to MIT and corresponding IPR NNH12AU04I to Lincoln Laboratory. awarded by the National Aeronautics and Space Administration. Work at Lincoln Laboratory was sponsored under Air Force Contract No. FA8721-05-6-0002. The Government has certain rights in the invention.

FIELD OF INVENTION

The invention relates to solid-state X-ray imagers, and, more particularly, to the integration of optical blocking filters directly onto the surface(s) of the detector.

BACKGROUND

While conventional x-ray imagers only display contrast in density, X-ray imaging spectrometers (XIS) enable extrapolation of the elemental composition of the material being imaged, as well. Such information is useful in manufacturing and medical diagnostics. One key challenge in using XIS in these applications includes making detectors insensitive to the visible light. Silicon detectors are commonly used for imaging X-ray due to their availability and low-noise. However, because silicon is also sensitive to visible light, an optical blocking filter is required to make silicon detectors insensitive to the visible light. If a visible light signal gets through the blocking filter, it will interfere with spectroscopy. Conventional blocking filters are fragile and challenging to integrate into the XIS.

XIS have been used in astronomy for many years. Conventional optical blocking filters, such as the ones used on the Chandra X-ray Observatory, which is one of the three National Aeronautics and Space Administration (NASA) great observatories, are free-standing. They are extremely thin because they have to permit X-ray transmission. The fragility of the filters adds significant challenge to the integration of such filters into the spectrometer and adds cost to the instrument. For space applications, the cost increase is even higher as a complicated chamber must be built around the spectrometer to protect the filters from the launch vibrations. In addition, the performance of free-standing filters cannot be optimized because the mechanical support layer, which typically comprises 200-nm polymer layer, reduces transmission of x-rays.

SUMMARY

An x-ray imaging device including an integrated optical blocking filter and methods for fabricating and using such a filter are described herein, where various embodiments of the apparatus and methods may include some or all of the elements, features and steps described below.

An x-ray imaging device, as described herein, can include an x-ray detector and an optical-blocking filter. The x-ray detector has an entrance-window surface for receiving x-rays, at least one side surface, and a back surface facing in an opposite direction from the entrance-window surface. The optical-blocking filter is deposited on and fully covers at least the entrance-window surface and the side surface of the x-ray detector, wherein the optical-blocking filter blocks visible (400-700 nm), ultraviolet (10-400 nm), and near-infrared (700-1,500 nm) light.

Herein, we describe a new way to integrate an optical blocking filter directly into the detector, which can lower cost and improve both durability and performance.

The scheme described herein can increases the robustness and performance of the optical blocking filter (OBF). The increased robustness can significantly decrease the weight and cost of the XIS. The described apparatus and methods are also applicable to other materials, such as Ge or HgCdTe X-ray detectors for high-energy X-ray detectors.

The direct deposition of aluminum on the detector substrate, and the method to minimize or reduce pin-holes reduce the potential for light leak into the detector; the side-wall deposition can stop or reduce light leak from the sides of the device; and the underside coating can stop or reduce light leak from the substrate.

The encapsulation of the detector in high optical density material thus can stop any light from causing noise in the detector. This technology also allows miniaturization and cost reduction for XIS.

By combining this technology with low-noise, high frame-rate CMOS imagers, X-ray imaging spectrometers can be commercialized in a wide-range of applications from medical imaging to scientific-research-analysis tools, in addition to enabling X-ray astronomy on smaller satellites. Another application for this technology is dental X-ray imaging. Currently, dental X-ray imaging provides density information of tissues via the contrast of X-rays transmitting through the tissue. The XIS apparatus and methods described herein can provide elemental-composition information of the tissues, as well, via X-ray fluorescence (XRF).

Another application for these apparatus and methods is the hand-held X-ray florescence (XRF) spectrometer. Handheld XRF has become the standard for non-destructive elemental analysis for applications ranging from alloy-composition verification to scrap metal valuation. Currently, silicon drift-detectors (SDD) and PIN diodes are used for XRF applications.

The x-ray imaging device can be capable of detecting and imaging a single photon. In particular embodiments, the optical-blocking filter further covers the back surface of the x-ray detector. In additional embodiments, the optical-blocking filter comprises aluminum.

The x-ray detector can be selected, e.g., from a charge-coupled device, a complementary metal-oxide semiconductor active-pixel sensor, a single diode, and a diode array.

In particular embodiments, the optical-blocking filter can block visible, ultraviolet, and near-infrared background light reaching the x-ray detector by a factor of at least 1 million.

Additionally, the optical-blocking filter can achieve full coverage of the entrance-window surface via deposition of an optical-blocking composition at a non-orthogonal angle to the entrance-window surface of the x-ray detector to reduce coverage gaps through which light can leak around particles on the entrance-window surface.

In particular embodiments, the x-ray imaging device is a spectrometer.

In a method for fabricating an x-ray imaging device, an x-ray detector is provided, wherein the x-ray detector has an entrance-window surface for receiving x-rays, at least one side surface, and a back surface facing in an opposite direction from the entrance-window surface. An optical-blocking composition is deposited to produce a coating of an optical-blocking filter on and fully covering at least the entrance-window surface and the side surface of the x-ray detector, wherein the optical-blocking filter blocks visible and ultraviolet light. In particular embodiments, the x-ray detector functions as a spectrometer.

In a method for portable x-ray detection, an x-ray imaging device, as described above, is transported to a remote site for x-ray detection. Then, x-rays received at the entrance-window surface of the x-ray imaging device are detected at the remote site while blocking interference from background visible and ultraviolet light with the optical-blocking filter. Then, the x-ray imaging device is further transported after the detection of x-rays.

In particular embodiments, the x-ray imaging device is a spectrometer and is transported into space aboard a spacecraft. In additional embodiments, the spectrometer is used to determine an elemental composition of a celestial object.

In alternative embodiments, the x-rays pass through at least a portion of a human body before being detected by the x-ray detector, the method further comprising generating a medical image from the detection. In particular embodiments, the medical image is a dental image.

In a particular exemplification, an optical-blocking filter (OBF) was directly deposited on entrance windows of high-performance CCDs for X-ray imaging spectrometer (XIS) application. It was found that the OBF does not degrade the performance of the CCDs. An aluminum OBF blocks out-of-band light in most of the pixels, but about 1% of the pixels are affected by pinholes. These pinholes can be successfully reduced by depositing aluminum at an angle. Light-leak through the side bond-line and near-IR through the substrate wafer is found to be significant for applications that require higher than $10^5$ extinction ratio. This light-leak path has been solved by employing side coatings and back-side metallization.

The integrated optical blocking filter enables miniaturization of XIS instruments, as it does not require protective housings. Therefore, this technology makes it possible to use XIS on cube satellites.

Figure 1:
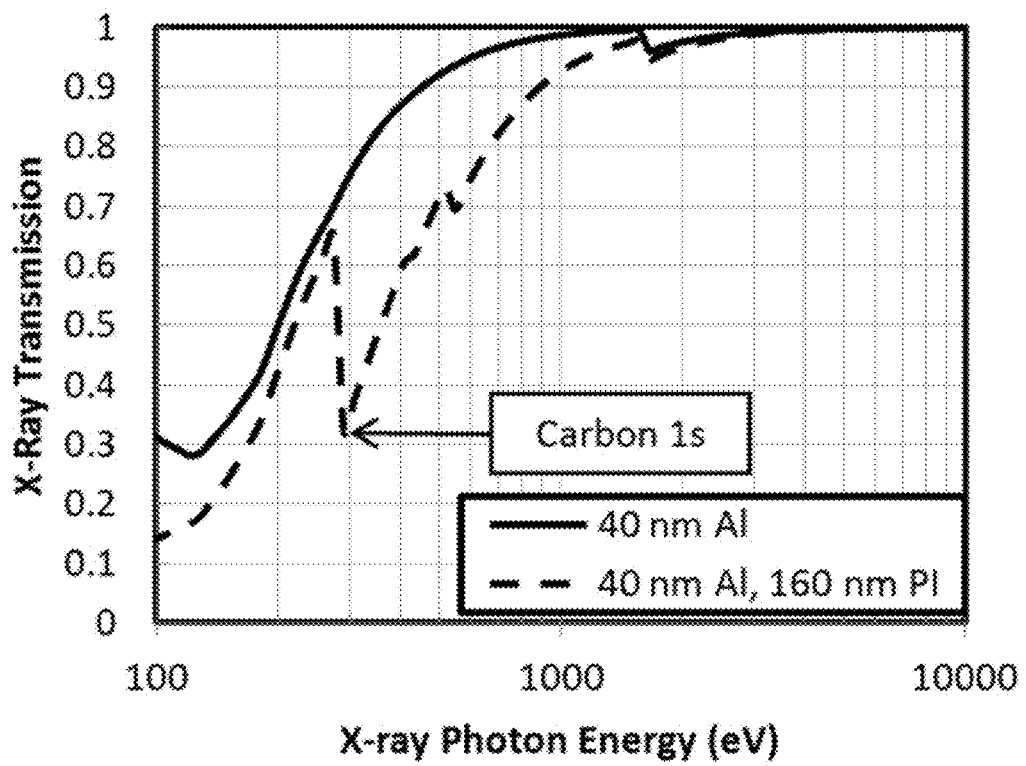
FIG. 1 shows simulated X-ray transmission for a free-standing filter versus a directly deposited filter.

In the accompanying drawings, like reference characters refer to the same or similar parts throughout the different views; and apostrophes are used to differentiate multiple instances of the same item or different embodiments of items sharing the same reference numeral. The drawings are not necessarily to scale; instead, an emphasis is placed upon illustrating particular principles in the exemplifications discussed below. For any drawings that include text (words, reference characters, and/or numbers), alternative versions of the drawings without the text are to be understood as being part of this disclosure; and formal replacement drawings without such text may be substituted therefor.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially (though not perfectly) pure, as practical and imperfect realities may apply; e.g., the potential presence of at least trace impurities (e.g., at less than 1 or 2%) can be understood as being within the scope of the description. Likewise, if a particular shape is referenced, the shape is intended to include imperfect variations from ideal shapes, e.g., due to manufacturing tolerances. Percentages or concentrations expressed herein can be in terms of weight or volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. The term, "about," means within ±10% of the value recited. In addition, where a range of values is provided, each subrange and each individual value between the upper and lower ends of the range is contemplated and therefore disclosed.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

Described below is an approach to integrate an optical blocking filter directly on the charge-coupled device (CCD) surface using standard thin-film deposition techniques, eliminating the need for fragile, free-standing filters. These filters do not require the heavy complex and expensive housing used in current instruments and can reduce mass, complexity, risk, and cost for a space mission, for example. Moreover, such filters can be thinner and result in better instrument sensitivity than free-standing ones. FIG. 1 shows X-ray transmission comparison of a free-standing filter that uses a 160-nm-thick polyimide layer (for mechanical support) with a 40-nm-thick aluminum coating (dashed line) versus a directly deposited optical blocking filter consisting of only 40-nm-thick aluminum (solid line). The X-ray transmission for the carbon is line is increased from 35% to over 75% for the directly deposited optical blocking filter (DD OBF) because the DD OBF does not require a mechanical support layer, as the CCD provides the support so the filter material and thickness can be freely optimized to match the filter performance requirement.

Reported herein are the results of applying a DD OBF on high-performance CCDs. We find that a DD OBF can be used with high-performance single-photon imaging X-ray spectrometers without paying a penalty in performance. There is no noticeable difference in the X-ray resolution from the CCDs with or without optical blocking filters on the entrance windows. In addition, we find that optical-blocking-filter performance matches theoretical expectations in both X-ray and optical transmission. The DD OBF can be applied to other detectors, such as a complementary metal-oxide-semiconductor active pixel sensor (CMOS APS), to enable low-cost x-ray imagers that can also perform single x-ray photon spectroscopy.

Methods and Process:

The directly deposited optical blocking filter (DD OBF) can be in the form of aluminum directly deposited on the detector surface. In one embodiment, thermal evaporation was used to deposit aluminum in high vacuum. During evaporation, the detector can be tilted so that the occurrence of pinholes from microscopic particles can be mitigated. Such pinholes can severely limit the usefulness of the detector.

In one embodiment, device wafers were loaded into the vacuum system, and the pressure was brought down to $7 \times 10^{-6}$ Torr. An aluminum source in a tungsten boat was heated to the aluminum evaporation temperature. The evaporation rate is typically 2 nm/sec, and 0.1% thickness non-uniformity was achieved over the imaging area of the CCD ($25 \times 25$ mm$^2$). Variable thicknesses of aluminum film are deposited for different optical blocking requirements; energized oxygen ions present in the vacuum chamber combine with the aluminum to form a 1-nm-thick $Al_2O_3$ layer to make the surface scratch-resistant. Two methods for depositing an optical blocking filter were developed for finished chips (i.e., those ready for electrical testing) and for an in-line wafer processing. For the finished chips, a precision shadow mask was developed to protect the CCD surface and the bondpads while allowing an optical-blocking filter (OBF) to be deposited over the entrance window. The placement accuracy of the shadow mask was ±250 µm, which allowed coverage of the serial registers of the CCDs without shorting the bondpads. This process allowed deposition on CCDs that were finished, allowing us to directly measure performance differences before and after OBF deposition.

The shadow mask was also modified to deposit on a portion of the CCD surface while leaving other parts unchanged, allowing direct comparison of the OBF-covered region to the region that did not have OBF covering at all. This selective deposition allowed a more direct comparison of the effect of the OBF on the performance of the CCD because the effect can be quantified on the same CCD. In the in-line process, the OBF was deposited before the silicon above the bondpads was etched to expose the bondpads. This approach offered a cleaner process, as the wafer surface was coming directly from a clean room into the vacuum system, allowing minimal opportunity for the surface to be contaminated with particles. The process also offered benefits from having the OBF patterned with 1-µm placement accuracy, as photolithography was used to pattern the OBF. Both methods were utilized extensively.

Figure 2:
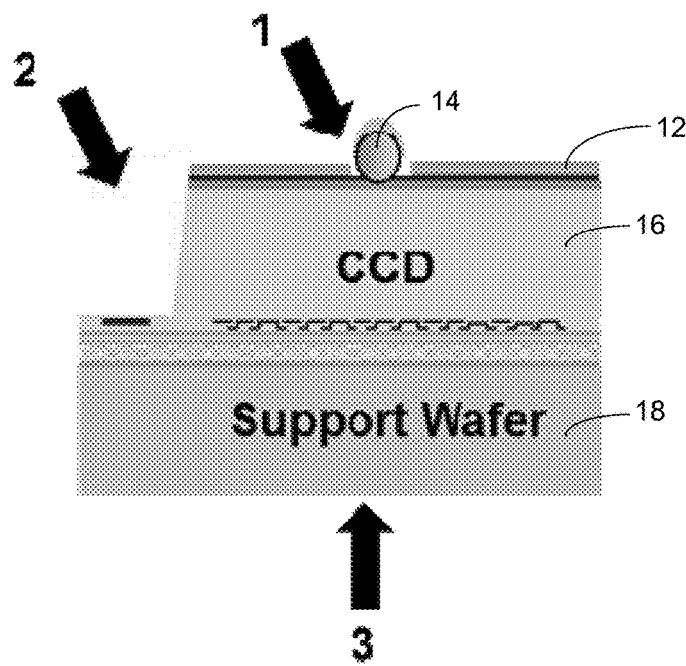
FIG. 2 schematically shows three pathways for light leak addressed herein for directly deposited optical blocking filters (DD OBFs). Each arrow shows a pathway for light leak. Pathway 1 is for light leak through pin-holes created by particles. Pathway 2 is for light leak through the side. Pathway 3 is for light leak through the substrate.

We also found that the contribution from edge and backside light leakage may be high enough to require additional mitigation methods for applications requiring a higher optical-extinction ratio. These light-leaks are addressed by edge and backside coatings. The three different light-leak paths 1 (through pinholes in the OBF 12 adjacent a particle 14), 2 (through the side edge of the CCD 16), and 3 (through backside of the support wafer 18) that can be mitigated via these methods are illustrated in FIG. 2.

Figure 3:
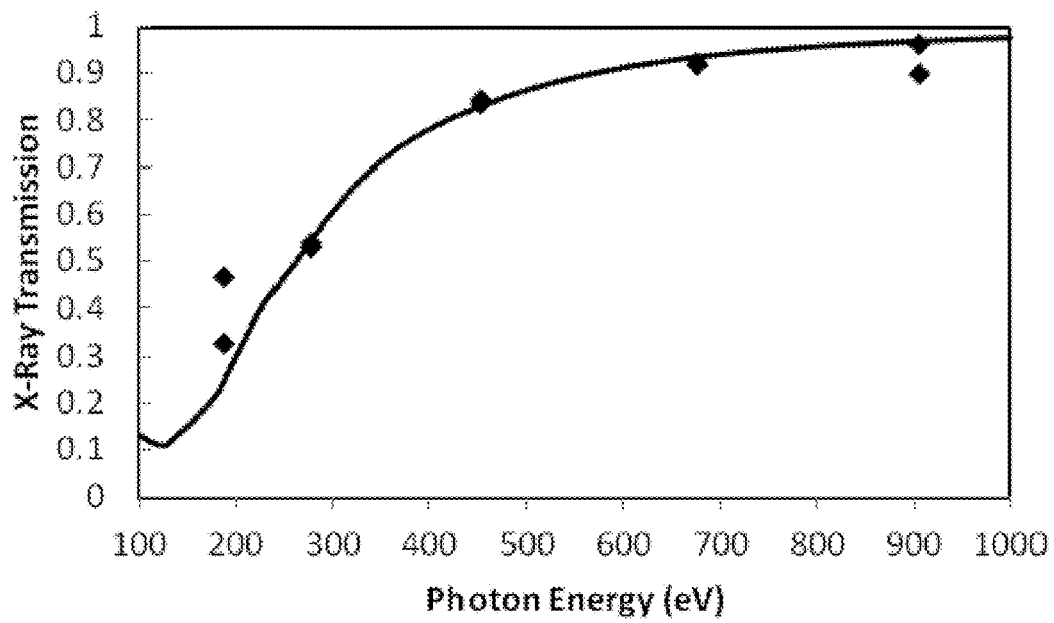
FIG. 3 plots the X-ray performance of an OBF in terms X-ray transmission measurements (diamonds) versus a model (line) for 70-nm-thick aluminum.

The transmission for 70-nm-thick aluminum over a range of photon energies is shown in FIG. 3 (with measurements shown as diamonds and the model plotted as the line), the plot of which also reflects theoretical expectations that verify that there is no heavy metal mixed into the optical blocking filter from the thermal evaporation process.

Figure 4:
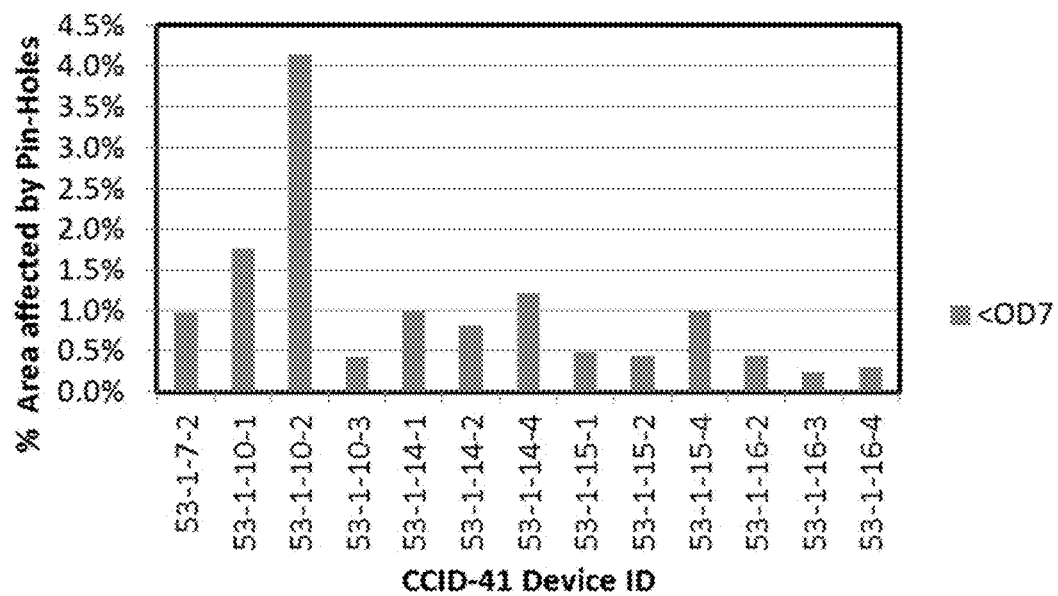
FIG. 4 plots the percent of pixels in which the extinction ratio was less than $10^7$ (<OD7) for 13 tested CCDs.

Pinholes were discovered during initial stages of characterization of the DD OBF. A small area of the device with a 220 nm-thick OBF was illuminated by a 633-nm HeNe laser. The total flux of the laser was characterized using a device without OBF and illuminating the surface with the laser through neutral-density filters in order to bring down the intensity to measurable levels. Through this measurement, the absorption coefficient of the aluminum in the region free of pinholes is $1.3 \times 10^6$ cm$^{-1}$, which is close to the literature value of $1.5 \times 10^6$ cm$^{-1}$ at 633 nm, as reported in A. D. Rakic, et al., "Optical Properties of Metallic Films for Vertical-Cavity Optoelectronic Devices," Appl. Opt., vol. 37, no. 22, pp. 5271-5283 (August 1998.) However, it also shows that some pixels have much higher transmission. To study the statistics of these pinholes, optical blocking power was characterized over the entire CCD using flood illumination with an LED and diffuser to illuminate the entire imaging area. A total of thirteen devices were characterized for screening devices. Due to the noise from long cables and limited cooling in the test set up, this set-up was capable of achieving an extinction ratio of $10^7$ (OD7). On average, about 1% of the pixels had an optical transmission with less than OD7. FIG. 4 shows the results of this evaluation for a plurality of CCDs indicated via their test identification numbers.

Figure 5:
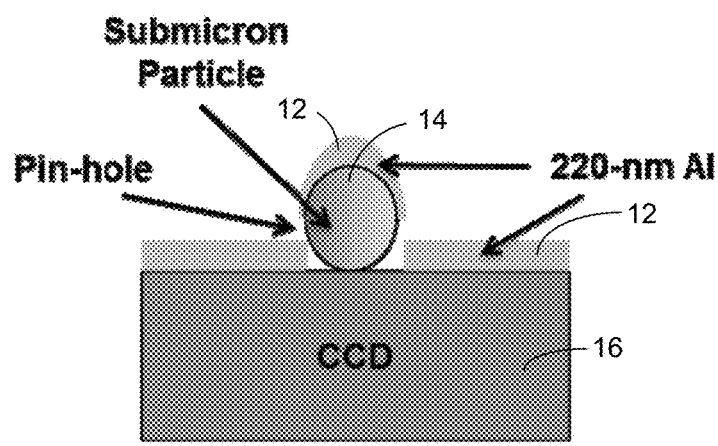
FIG. 5 is an illustration of how pinholes are created by surface irregularities or a particle, wherein a particle that is thicker than the thickness of the OBF leaves a tiny pinhole on the side of the particle due to the directionality of the vacuum-evaporated-aluminum-deposition process.
Figure 6:
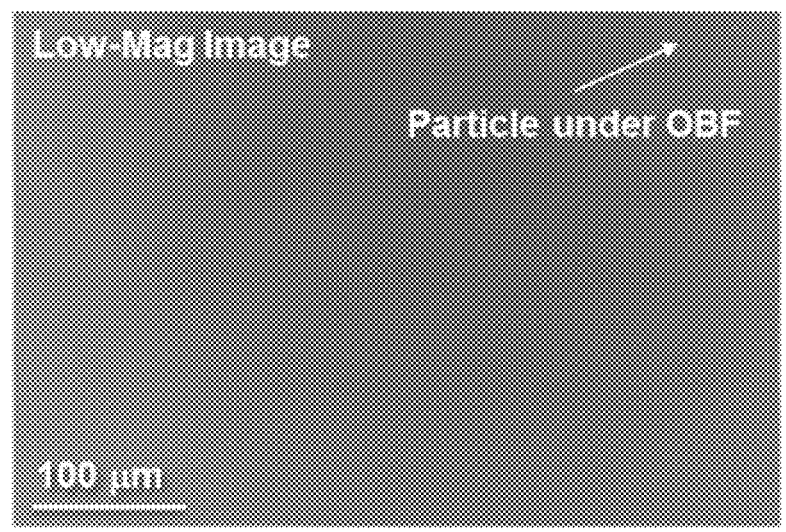
FIGS. 6 and 7 are scanning-electron-microscope (SEM) images of the surface of a CCD with an OBF. The image of FIG. 6 shows a low-magnification image of an area covering over 100 pixels; one particle is found for this field of view. The high-magnification image of FIG. 7 shows that the sub-micron pinholes form around the edge of the particle; about 1% of the pixels studied have these surface irregularities with pinholes.
Figure 7:
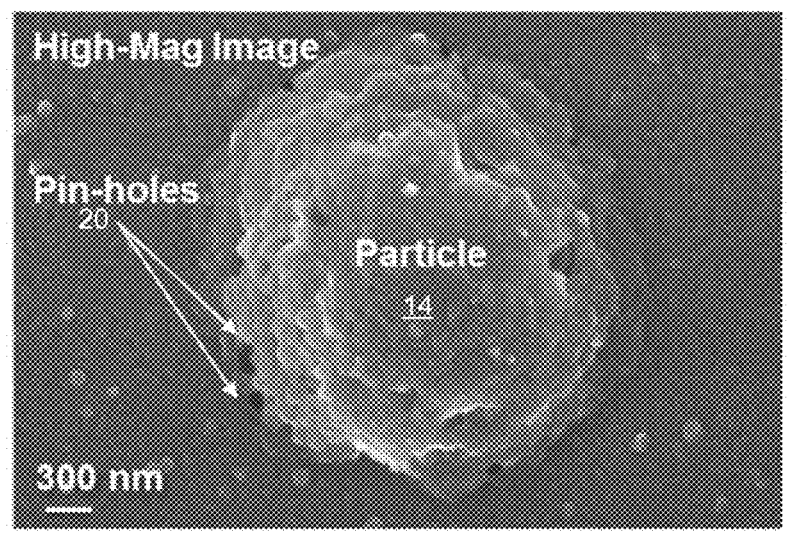

It is likely that particles or surface irregularities present on the detector surface before the OBF is deposited are the cause of the pinholes. It is thought that because thermally evaporated aluminum is highly directional, if the particle is larger than the thickness of the aluminum, the particle will lead to a pin hole adjacent to the particle, as illustrated in FIG. 5. A pinhole as small as 24×24 nm can cause a light leak to limit the extinction ratio to OD6 for the entire pixel, which is 24×24 µm large. To verify this claim, scanning-microscope images were taken of CCDs with the optical-blocking filter. The scanning-microscope images found surface irregularities covering about 1% of the pixels sampled. Some of the captured SEM images are shown in FIGS. 6 and 7. The magnified view of FIG. 7 shows the presence of pinholes 20 (adjacent the particle 14) due to surface irregularities.

Figure 8:
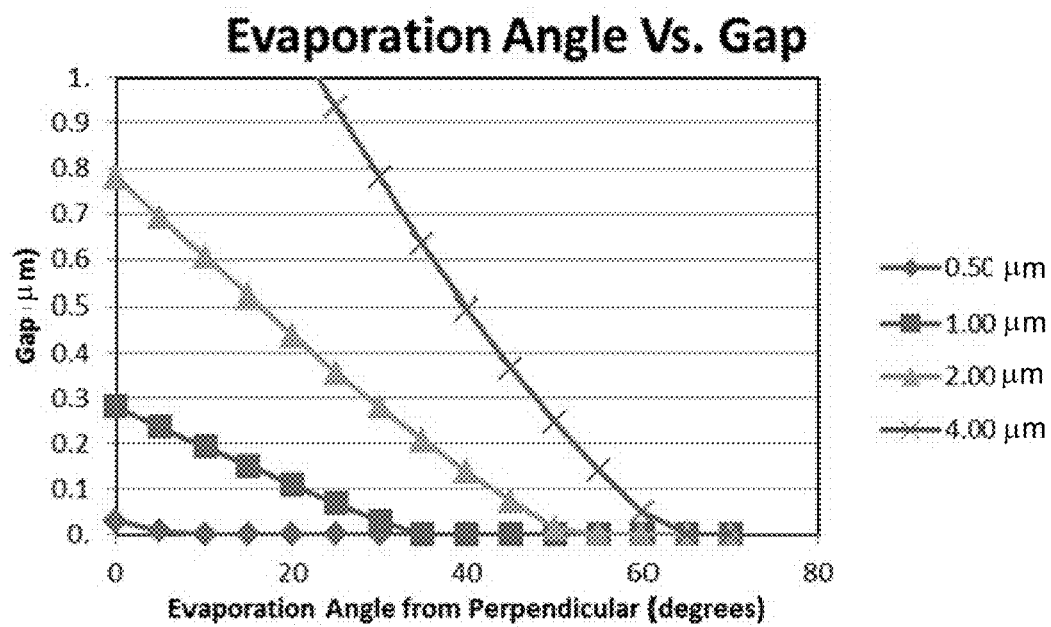
FIG. 8 is a plot of the gap versus deposition angle for a 220-nm-thick OBF for various size particles.

Modeling the particle with spherical geometry and vacuum deposition of aluminum as being perfectly directional, a particle larger than twice the thickness of the OBF leads to a pinhole that increases with the size of the particle. Depositing the aluminum from an oblique angle allows coverage of the side-wall of the particle. Such a relationship is expressed in the following equation: $\text{Gap} = R*(1 - \sin(\theta)) - T$, where R is the radius of the particle; θ is the deposition angle from perpendicular; and T is the thickness of the OBF. FIG. 8 plots the gap (in µm) versus the deposition angle for various sizes of particles when the CCD receives a 220-nm-thick OBF. At a deposition angle of 45°, particles smaller than 1 µm result in no gaps. Surface measurements were performed on CCD wafers prior to OBF deposition. Particles smaller than 1 µm were the majority of the particles on the surface of the CCD.

Figure 9:
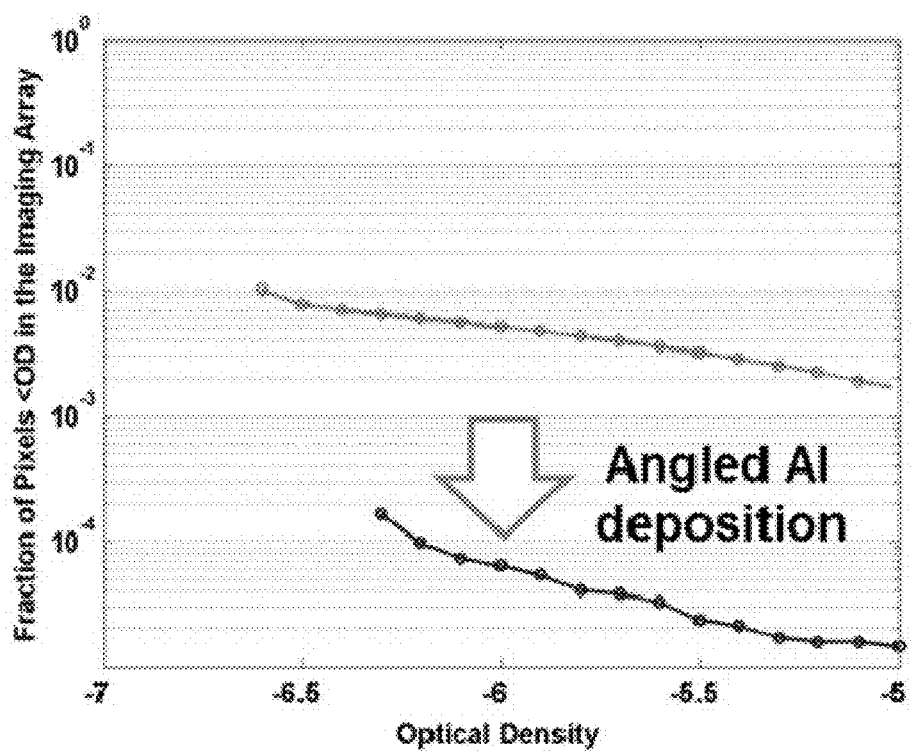
FIG. 9 is a plot showing the reduction of pinhole population after angled deposition. A device with a 220-nm-thick aluminum OBF was characterized. Subsequently, additional 100-nm-thick aluminum was deposited and characterized again, after which the density of pinholes dropped by approximately 100 times.

Following this analysis, aluminum was deposited at 45° to cover the sidewall of the particles. This angled deposition was accomplished by tilting the stage to which the devices are attached during aluminum deposition. During the deposition, the stage was rotated to cover all sides of the particles. The angled deposition resulted in a significant reduction of the pinhole population (lower plot), as shown in FIG. 9.

Figures 10, 11:
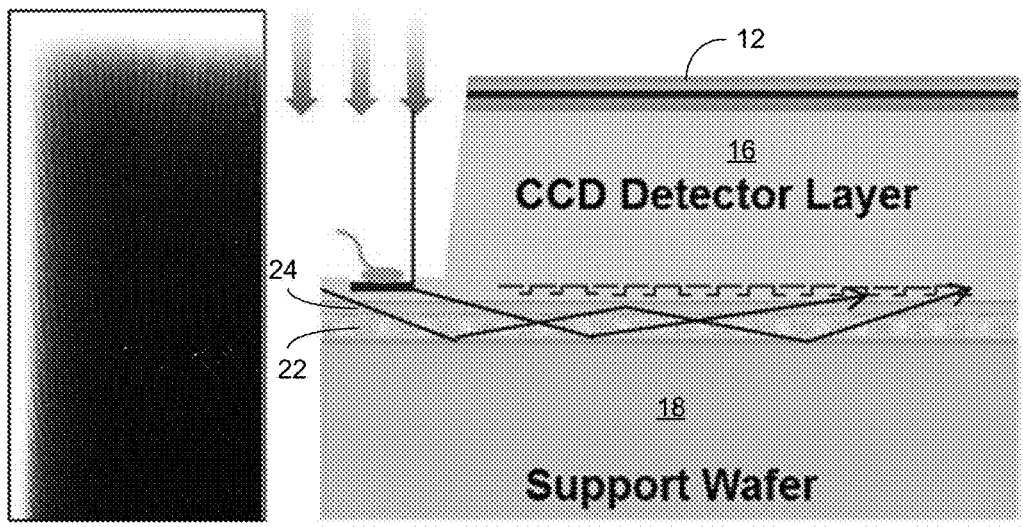
FIG. 10 shows a CCD detector with a directly-deposited blocking filter under flood illumination of white light; white areas around the edges have attenuation <$10^7$ and are due to light entering the sides of the detector.
FIG. 11 is an illustration of light leakage paths, wherein the oxide and epoxy bond-line act as a path for which the light can travel to the center of the CCD with relatively little attenuation.
Figure 12:
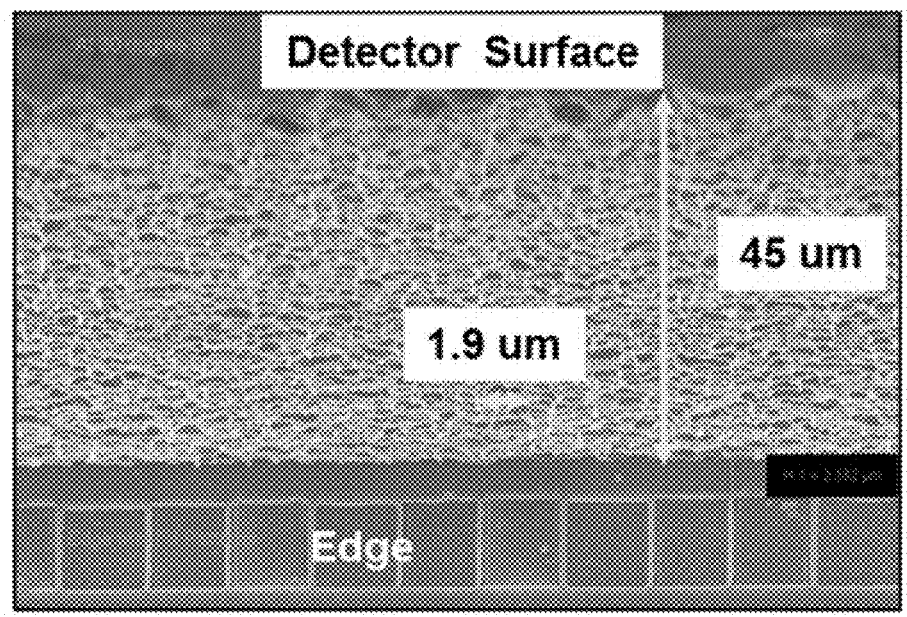
FIG. 12 is an SEM image of the edge of the CCD showing roughness in the sidewall and edge, which enhances light coupling into the bond-line.

For applications requiring a high visible-light-extinction ratio of >$10^9$, we found that the light leak from the edge of the CCD significantly reduces the usable area when the silicon side walls are left uncoated, as shown in FIGS. 10-12. FIG. 10 shows light leak in a CCD detector with a directly-deposited blocking filter under flood illumination of white light. White areas around the edges have attenuation <$10^7$ and are due to light entering the sides of the detector. FIG. 11 is an illustration of light leakage paths into the CCD 16. The oxide 22 and epoxy bond-line 24 act as a path for which the light can travel to the center of the CCD 16 with relatively little attenuation. FIG. 12 is a scanning-electron-microscope (SEM) image of the edge of the CCD, showing roughness in the sidewall and edge, which enhances light coupling into the bond-line.

Through SEM images, we found that there is significant edge roughness in the regions where mesa walls were removed via plasma etching. Micrometer-thick material was deposited on the edges to stop the light leak. A process to coat the sidewalls with space-qualified low-outgassing AEROGLAZE Z307 polyurethane paint (manufactured for Socomore by Lord Corporation of Saegertown, Pa., US) was developed. The paint did not cover the region 200 µm from the mesa edge to stop the paint from covering the entrance window. If the entrance window were to be covered with the polyurethane paint, the paint would stop most X-rays from reaching the CCD, as the paint coating is tens of micrometers thick. A process was developed wherein a uniform thickness of paint was applied on each side of the CCD. The process utilized spacer layers that created a puddle of paint that is uniformly 100-µm thick. The CCD was dipped into the 100-µm-deep puddle creating a uniform coating of the sidewalls that does not encroach on the surface by more than 100 µm.

Figure 13:
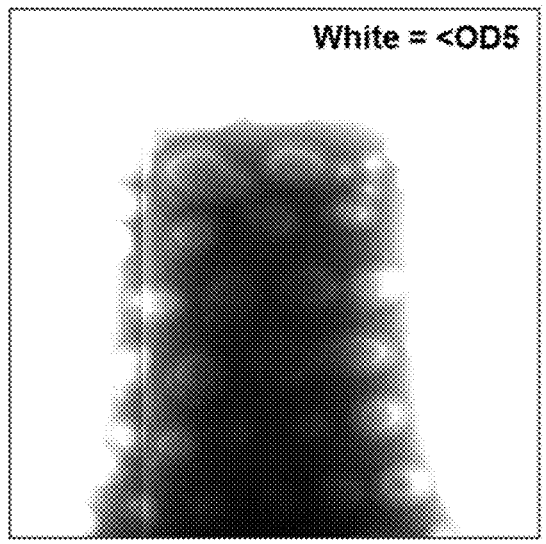
FIG. 13 shows near-IR ($\lambda=1,000$ nm) transmission through a substrate wafer for a CCD without an underside coating; the image is scaled so that white regions indicate less than $10^5$ attenuation.
Figure 14:
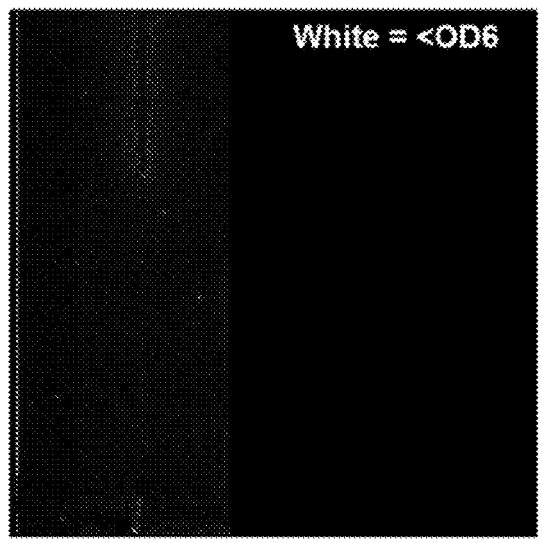
FIG. 14 shows near-IR ($\lambda=1,000$ nm) transmission through a substrate wafer for a CCD with an underside coating of 300 nm of aluminum. The image is scaled so that white regions indicate less than $10^6$ attenuation, evidencing that there is no perceptible light leak.
Figure 15:
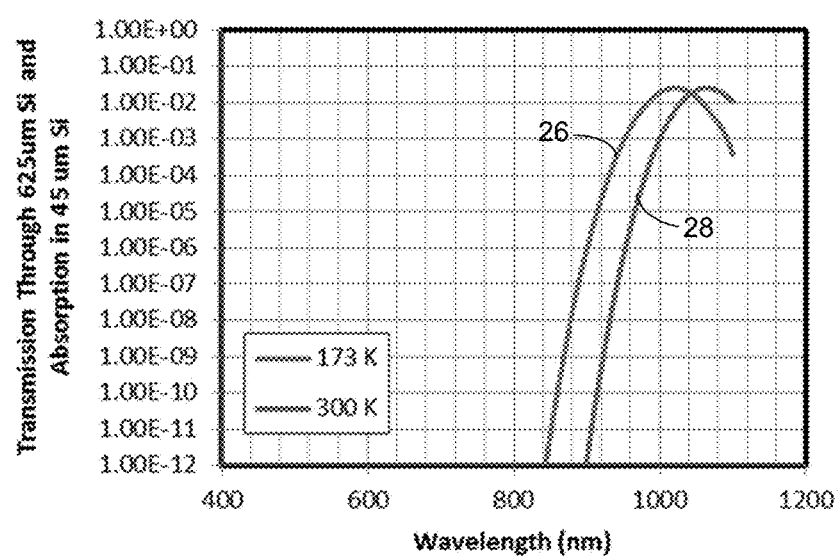
FIG. 15 is a plot of the calculation of silicon light leak through the handle silicon wafer at various wavelengths for CCD operation temperatures of 173 K and 300 K. At its peak, the total absorption of light at 1,000 nm through the back is 0.1~2%, which is equivalent to attenuation of $10^3$ to $10^2$.

Lastly, there is significant near-IR (NIR) light that penetrates through the handle wafer that creates problems for applications requiring an extinction ratio of $10^3$ or higher for that waveband of light. FIG. 13 shows a CCD leaking light through the substrate (with no coating). Analysis shows that although only a small fraction of light at 1,000 nm gets absorbed; at this wavelength, the absorption length is sufficiently long to go through the handle silicon wafer yet short enough to allow some of the light to be collected. As shown in FIG. 15, the amount of light that goes through the support wafer and that is absorbed in the detector layer peaks between 1,000-1,100 nm, depending on CCD operation temperatures (173 K as plot 26 and 300K as plot 28. At its peak, the total absorption of light at 1,000 nm through the back is 0.1~2%, which is equivalent to an extinction ratio of $10^3$ to $10^2$. To mitigate this problem, a new process to coat the back side (underside) of the CCDs was developed. Two separate processes were developed. One process used the AEROGLAZE Z307 polyurethane paint, and the other process used 300-nm-thick aluminum. Both films were TVAC tested for adhesion with the ceramic to which the CCDs are bonded. Both materials passed the TVAC test. Ultimately, aluminum was chosen for repeatability and flatness. After application of the back-side coating, the device was characterized again. As shown in FIG. 14, the back-side coating on the support wafer reduced the light leak through the support wafer at 1,000 nm.

It is expected that these methods and apparatus will be useful for future X-ray imaging spectrometer (XIS) instruments. The methods and apparatus can lower the hurdle for making compact single-photon sensitive X-ray imaging detectors for space, medical, and material inspection applications. The methods and apparatus can be combined with low-noise, fast-frame CMOS imagers to enable x-ray imaging spectroscopy for medical radiographs or analysis of metals, including compositions of carbon. The DD OBF on a sensitive detector can provide single x-ray photon sensitivity by removing background noise, and thereby may lower the total dose required to form a diagnostic image. In addition, the invention can be used to provide x-ray fluorescence imaging of materials down to the scale of carbon atoms.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step. Likewise, a single element or step may be replaced with a plurality of elements or steps that serve the same purpose. Further, where parameters for various properties or other values are specified herein for embodiments of the invention, those parameters or values can be adjusted up or down by 1/100th, 1/50th, 1/20th, 1/10th, 1/5th, 1/3rd, 1/2, 2/3rd, 3/4th, 4/5th, 9/10th, 19/20th, 49/50th, 99/100th, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions, and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety for all purposes; and all appropriate combinations of embodiments, features, characterizations, and methods from these references and the present disclosure may be included in embodiments of this invention. Still further, the components and steps identified in the Background section are integral to this disclosure and can be used in conjunction with or substituted for components and steps described elsewhere in the disclosure within the scope of the invention. In method claims (or where methods are elsewhere recited), where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. An x-ray imaging device, comprising:
   an x-ray detector having an entrance-window surface for receiving x-rays, at least one side surface, and a back surface facing in an opposite direction from the entrance-window surface; and
   an optical-blocking filter deposited on and fully covering at least the entrance-window surface and the side surface of the x-ray detector, wherein the optical-blocking filter blocks visible, ultraviolet, and near-infrared light.

2. The x-ray imaging device of claim 1, wherein the optical-blocking filter further covers the back surface of the x-ray detector.

3. The x-ray imaging device of claim 1, wherein the optical-blocking filter comprises aluminum.

4. The x-ray imaging device of claim 1, wherein the x-ray detector is selected from a charge-coupled device, a complementary metal-oxide semiconductor active-pixel sensor, a single diode, and a diode array.

5. The x-ray imaging device of claim 1, wherein the optical-blocking filter blocks visible, ultraviolet, and near-infrared background light reaching the x-ray detector by a factor of at least 1 million.

6. The x-ray imaging device of claim 1, wherein the optical-blocking filter achieves full coverage of the entrance-window surface via deposition of an optical-blocking composition at a non-orthogonal angle to the entrance-window surface of the x-ray detector to reduce coverage gaps through which light can leak around particles on the entrance-window surface.

7. The single-photon x-ray imaging device of claim 1, wherein the x-ray imaging device is a spectrometer.

8. A method for fabricating an x-ray imaging device, comprising:
   providing an x-ray detector having an entrance-window surface for receiving x-rays, at least one side surface, and a back surface facing in an opposite direction from the entrance-window surface; and
   depositing an optical-blocking composition to produce a coating of an optical-blocking filter on and fully covering at least the entrance-window surface and the side surface of the x-ray detector, wherein the optical-blocking filter blocks visible and ultraviolet light.

9. The method of claim 8, further comprising depositing the optical-blocking composition on the back surface of the x-ray detector.

10. The method of claim 8, wherein the optical-blocking composition is deposited at a non-orthogonal angle to the entrance-window surface of the x-ray detector to reduce coverage gaps through which light can leak around particles on the entrance-window surface.

11. The method of claim 8, wherein the optical-blocking filter comprises aluminum.

12. The method of claim 8, wherein the x-ray detector is selected from a charge-coupled device, a complementary metal-oxide semiconductor active-pixel sensor, a single diode, and a diode array.

13. The method of claim 8, wherein the x-ray detector functions as a spectrometer.

14. The method of claim 8, wherein the optical-blocking filter blocks visible and ultraviolet background light reaching the x-ray detector by a factor of at least 1 million.

15. A method for portable x-ray detection, comprising:
providing an x-ray imaging device, comprising an x-ray detector having an entrance-window surface for receiving x-rays, at least one side surface, and a back surface facing in an opposite direction from the entrance-window surface; and an optical-blocking filter deposited on and fully covering at least the entrance-window surface and the side surface of the x-ray detector;
transporting the x-ray imaging device to a remote site for x-ray detection; then
detecting x-rays received at the entrance-window surface of the x-ray imaging device at the remote site while blocking interference from background visible and ultraviolet light with the optical-blocking filter; and then
further transporting the x-ray imaging device after the detection of x-rays.

16. The method of claim 15, wherein the x-ray imaging device is a spectrometer and is transported into space aboard a spacecraft.

17. The method of claim 16, further comprising using the spectrometer to determine an elemental composition of a celestial object.

18. The method of claim 15, wherein the x-rays pass through at least a portion of a human body before being detected by the x-ray detector, the method further comprising generating a medical image from the detection.

19. The method of claim 18, wherein the medical image is a dental image.

20. The method of claim 15, wherein the optical-blocking filter blocks visible and ultraviolet background light reaching the x-ray detector by a factor of at least 1 million.

* * * * *